(12) United States Patent
Kinsella

(10) Patent No.: US 10,540,913 B2
(45) Date of Patent: Jan. 21, 2020

(54) SURGICAL SIMULATOR

(71) Applicant: Medalus Inc, Los Altos, CA (US)

(72) Inventor: Christopher Kinsella, Los Altos, CA (US)

(73) Assignee: MEDALUS INC., Los Altos, CA (US)

( * ) Notice: Subject to any disclaimer, the term of this patent is extended or adjusted under 35 U.S.C. 154(b) by 130 days.

(21) Appl. No.: 15/665,615

(22) Filed: Aug. 1, 2017

(65) Prior Publication Data

US 2017/0330488 A1 Nov. 16, 2017

Related U.S. Application Data

(60) Provisional application No. 62/371,434, filed on Aug. 5, 2016.

(51) Int. Cl.
*G09B 23/28* (2006.01)
*G09B 23/30* (2006.01)
*A61B 17/12* (2006.01)
*A61M 25/04* (2006.01)

(52) U.S. Cl.
CPC ........ *G09B 23/30* (2013.01); *A61B 17/12022* (2013.01); *A61M 25/04* (2013.01); *G09B 23/285* (2013.01)

(58) Field of Classification Search
CPC ...... G09B 23/28; G09B 23/285; G09B 23/30; G09B 23/303
USPC .......................... 434/262, 267, 268, 272, 274
See application file for complete search history.

(56) References Cited

U.S. PATENT DOCUMENTS

| | | | |
|---|---|---|---|
| 3,027,655 A | 4/1962 | Alderson | |
| 4,773,865 A | 9/1988 | Baldwin | |
| 5,620,326 A | 4/1997 | Younker | |
| 5,634,797 A * | 6/1997 | Montgomery | ....... G09B 23/286 434/268 |
| 6,062,866 A | 5/2000 | Prom | |

(Continued)

FOREIGN PATENT DOCUMENTS

| | | |
|---|---|---|
| WO | 16044577 A1 | 3/2016 |
| WO | 17074176 A1 | 5/2017 |
| WO | 2017123655 A1 | 7/2017 |

OTHER PUBLICATIONS

Andersen et al., "Pre-Hospital Resuscitative Endovascular Balloon Occlusion of the Aorta", Scandinavian Journal of Trauma, Resuscitation and Emergency Medicine, 2014, pp. P19, vol. 22, No. 1.

(Continued)

*Primary Examiner* — Kurt Fernstrom
(74) *Attorney, Agent, or Firm* — Greensfelder, Hemker & Gale, P.C.

(57) ABSTRACT

A mannequin has a torso portion with a simulated vertebral column and anatomical aortic zones for the REBOA procedure. A fluid pressure source provides a fluid to the torso portion, and a fluid collection reservoir receives fluid from the torso portion. Conduits extend between the fluid pressure source and collection reservoir. Valves associated with the conduits and the fluid pressure source and collection reservoir may be positioned to simulate injuries in the first, second and third REBOA zones. A main conduit simulates the aorta. A simulated groin portion is configured to receive a REBOA catheter. The simulated groin portion has a conduit simulating the femoral artery.

18 Claims, 7 Drawing Sheets

(56) References Cited

U.S. PATENT DOCUMENTS

| | | | |
|---|---|---|---|
| 6,234,804 B1 | 5/2001 | Yong | |
| 6,790,043 B2 | 9/2004 | Aboud | |
| 7,021,940 B2 | 4/2006 | Morris et al. | |
| 7,798,815 B2 | 9/2010 | Ramphal et al. | |
| 7,887,330 B2 | 2/2011 | King | |
| 8,556,635 B2* | 10/2013 | Toly | G09B 23/30 434/262 |
| 9,342,997 B2 | 5/2016 | Feins et al. | |
| 9,424,760 B2* | 8/2016 | Ghez | G09B 23/32 |
| 2009/0011394 A1 | 1/2009 | Meglan et al. | |
| 2009/0130643 A1 | 5/2009 | Cusano | |
| 2009/0226867 A1* | 9/2009 | Kalafut | G09B 23/32 434/268 |
| 2010/0196865 A1* | 8/2010 | Kays | G09B 23/32 434/268 |
| 2010/0323339 A1 | 12/2010 | Ritchie | |
| 2011/0217684 A1 | 9/2011 | Park et al. | |
| 2013/0203032 A1* | 8/2013 | Bardsley | G09B 23/30 434/268 |
| 2016/0140878 A1 | 5/2016 | Fernandez | |

OTHER PUBLICATIONS

Keller et al., "Design of a Cost Effective, Hemodynamically Adjustable Model for Resuscitative Endovascular Balloon Occlusion of the Aorta (REBOA) Simulation", Journal of Trauma and Acute Care Surgery, Sep. 2016, pp. 606-611, vol. 81, No. 3.

Lendrum et al., "A Training Package for Zone III Resuscitative Endovascular Balloon Occlusion of the Aorta (REBOA)", Scandinavian Journal of Trauma, Resuscitation adn Emergency Medicine, 2014, pp. P18, vol. 22, No. 1.

* cited by examiner

SURGICAL SIMULATOR

CROSS REFERENCE TO RELATED APPLICATIONS

This application is a U.S. Non-Provisional Application which claims the benefit of U.S. Provisional Appl. No. 62/371,434 filed on Aug. 5, 2016

SUMMARY

This disclosure relates to surgical simulators. More particularly, this disclosure relates to a surgical simulator for the Resuscitative Endovascular Balloon Occlusion of the Aorta (REBOA) procedure.

DETAILED DESCRIPTION

Figure 1:
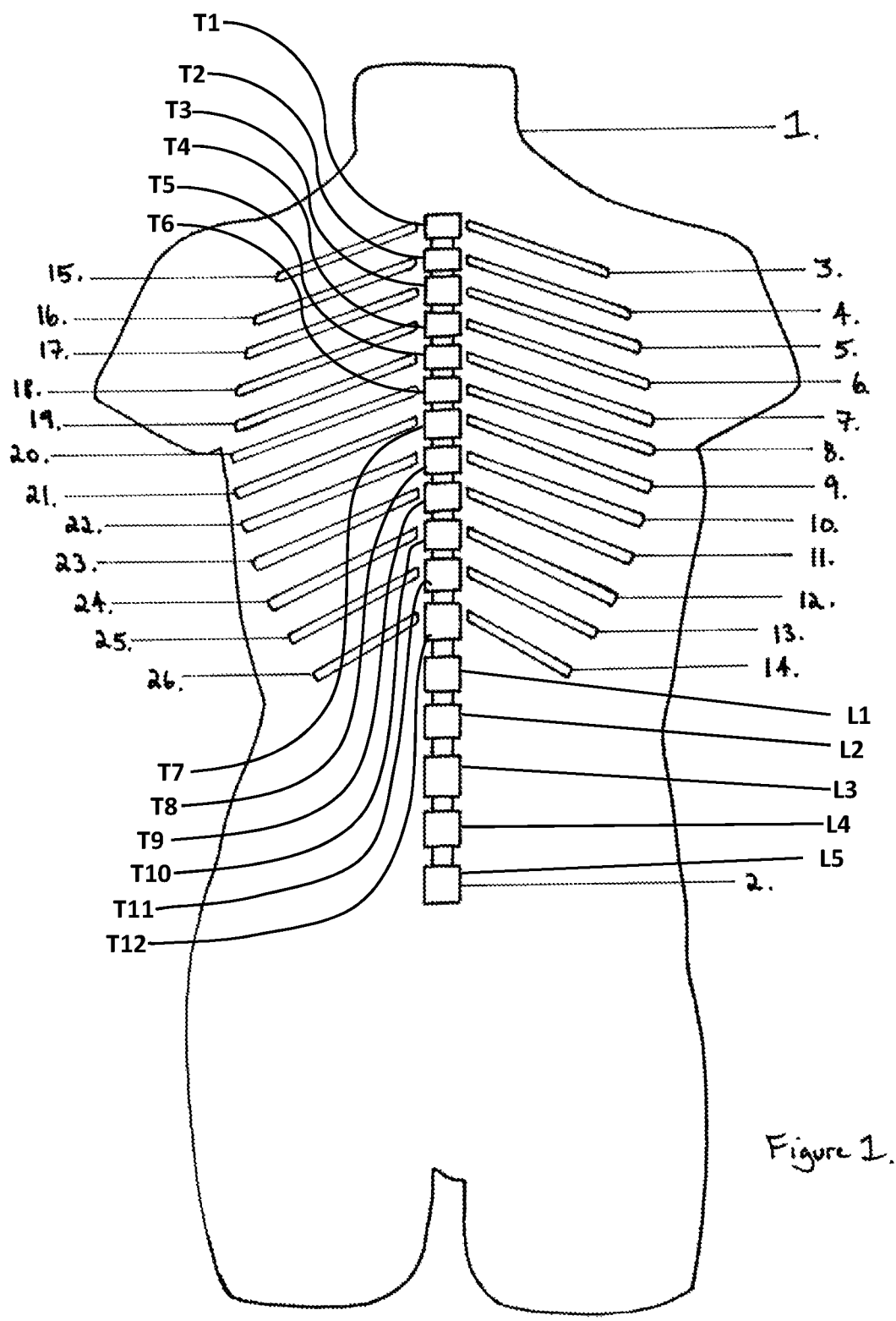
FIG. 1 depicts an embodiment of a model backing having radiographic landmarks according to the present disclosure.

This disclosure relates to surgical simulators, and more particularly, to a surgical simulator for the Resuscitative Endovascular Balloon Occlusion of the Aorta (REBOA) procedure. The exemplary simulator provides appropriate haptic feedback and simulates the physical presence of the patient. The exemplary simulator simulates percutaneous needle access, ultrasound guided percutaneous access, and surgical access of the femoral vessels. The exemplary simulator allows for training of the medical professional on how to manage the materials and operative space in a real life scenario.

The exemplary simulator replicates physical aspects of a patient for REBOA and includes a form of the patient having femoral vessels, which can be accessed in clinically relevant methods, as well as verification of correct placement and occlusion of the aorta in an analog manner (e.g., the simulator stops "bleeding") and in an objective manner (e.g., via roentgenogram or fluoroscopic verification of balloon placement). The simulator is maintained and operated without the need for electronics.

In an exemplary embodiment, the device may include a polypropylene sheet (1), ⅛" thick, cut to form silhouette of a torso.

In an exemplary embodiment, the device may include central tube (simulated vertebral column) (2) of dense, partially radio-opaque material such as polyvinyl chloride to mimic position of spinal column and to provide position reference on roentgenogram. The central tube (simulated vertebral column) may be approximately 51 millimeters in outer diameter, with three quarters circumference sections removed at intervals from 27 millimeters to 21 millimeters to mimic the intervertebral joint spaces of the lumbar and thoracic spine. The uncut sections correspond to Thoracic vertebral bodies T1-T12 and Lumbar vertebral bodies L1-L5. The sections with three-quarters circumference removed correspond to the intervertebral disc spaces.

In an exemplary embodiment, the device may include clear polyvinyl chloride tubing (simulated rib) (3) ⅜" inner diameter, ½" outer diameter, length 7 cm in length, with medial aspect centered at section of component 2 corresponding to positions T1.

In an exemplary embodiment, the device may include clear polyvinyl chloride tubing (simulated rib) (4) ⅜" inner diameter, ½" outer diameter, length 9 cm in length, with medial aspect centered at section of component 2 corresponding to positions T2.

In an exemplary embodiment, the device may include clear polyvinyl chloride tubing (simulated rib) (5) ⅜" inner diameter, ½" outer diameter, length 11 cm in length, with medial aspect centered at section of component 2 corresponding to positions T3.

In an exemplary embodiment, the device may include clear polyvinyl chloride tubing (simulated rib) (6) ⅜" inner diameter, ½" outer diameter, length 12.5 cm in length, with medial aspect centered at section of component 2 corresponding to positions T4.

In an exemplary embodiment, the device may include clear polyvinyl chloride tubing (simulated rib) (7) ⅜" inner diameter, ½" outer diameter, length 13 cm in length, with medial aspect centered at section of component 2 corresponding to positions T5.

In an exemplary embodiment, the device may include clear polyvinyl chloride tubing (simulated rib) (8) ⅜" inner diameter, ½" outer diameter, length 13 cm in length, with medial aspect centered at section of component 2 corresponding to positions T6.

In an exemplary embodiment, the device may include clear polyvinyl chloride tubing (simulated rib) (9) ⅜" inner diameter, ½" outer diameter, length 13 cm in length, with medial aspect centered at section of component 2 corresponding to positions T7.

In an exemplary embodiment, the device may include clear polyvinyl chloride tubing (simulated rib) (10) ⅜" inner diameter, ½" outer diameter, length 12.5 cm in length, with medial aspect centered at section of component 2 corresponding to positions T8.

In an exemplary embodiment, the device may include clear polyvinyl chloride tubing (simulated rib) (11) ⅜" inner diameter, ½" outer diameter, length 11.5 cm in length, with medial aspect centered at section of component 2 corresponding to positions T9.

In an exemplary embodiment, the device may include clear polyvinyl chloride tubing (simulated rib) (12) ⅜" inner diameter, ½" outer diameter, length 10 cm in length, with medial aspect centered at section of component 2 corresponding to positions T10.

In an exemplary embodiment, the device may include clear polyvinyl chloride tubing (simulated rib) (13) ⅜" inner diameter, ½" outer diameter, length 8.5 cm in length, with medial aspect centered at section of component 2 corresponding to positions T11.

In an exemplary embodiment, the device may include clear polyvinyl chloride tubing (simulated rib) (14) ⅜" inner diameter, ½" outer diameter, length 7 cm in length, with medial aspect centered at section of component 2 corresponding to positions T12.

In an exemplary embodiment, the device may include clear polyvinyl chloride tubing (simulated rib) (15) ⅜" inner diameter, ½" outer diameter, length 7 cm in length, with medial aspect centered at section of component 2 corresponding to positions T1.

In an exemplary embodiment, the device may include clear polyvinyl chloride tubing (simulated rib) (16) ⅜" inner diameter, ½" outer diameter, length 9 cm in length, with medial aspect centered at section of component 2 corresponding to positions T2.

In an exemplary embodiment, the device may include clear polyvinyl chloride tubing (simulated rib) (17) ⅜" inner diameter, ½" outer diameter, length 11 cm in length, with medial aspect centered at section of component 2 corresponding to positions T3.

In an exemplary embodiment, the device may include clear polyvinyl chloride tubing (simulated rib) (18) ⅜" inner diameter, ½" outer diameter, length 12.5 cm in length, with medial aspect centered at section of component 2 corresponding to positions T4.

In an exemplary embodiment, the device may include clear polyvinyl chloride tubing (simulated rib) (19) ⅜" inner diameter, ½" outer diameter, length 13 cm in length, with medial aspect centered at section of component 2 corresponding to positions T5.

In an exemplary embodiment, the device may include clear polyvinyl chloride tubing (simulated rib) (20) ⅜" inner diameter, ½" outer diameter, length 13 cm in length, with medial aspect centered at section of component 2 corresponding to positions T6.

In an exemplary embodiment, the device may include clear polyvinyl chloride tubing (simulated rib) (21) ⅜" inner diameter, ½" outer diameter, length 13 cm in length, with medial aspect centered at section of component 2 corresponding to positions T7.

In an exemplary embodiment, the device may include clear polyvinyl chloride tubing (simulated rib) (22) ⅜" inner diameter, ½" outer diameter, length 12.5 cm in length, with medial aspect centered at section of component 2 corresponding to positions T8.

In an exemplary embodiment, the device may include clear polyvinyl chloride tubing (simulated rib) (23) ⅜" inner diameter, ½" outer diameter, length 11.5 cm in length, with medial aspect centered at section of component 2 corresponding to positions T9.

In an exemplary embodiment, the device may include clear polyvinyl chloride tubing (simulated rib) (24) ⅜" inner diameter, ½" outer diameter, length 10 cm in length, with medial aspect centered at section of component 2 corresponding to positions T10.

In an exemplary embodiment, the device may include clear polyvinyl chloride tubing (simulated rib) (25) ⅜" inner diameter, ½" outer diameter, length 8.5 cm in length, with medial aspect centered at section of component 2 corresponding to positions T11.

In an exemplary embodiment, the device may include clear polyvinyl chloride tubing (simulated rib) (26) ⅜" inner diameter, ½" outer diameter, length 7 cm in length, with medial aspect centered at section of component 2 corresponding to positions T12.

In an exemplary embodiment, the device may include superior surface (27) of silicone groin mold (simulated groin), with curvilinear surface to mimic the folds of the human groin.

In an exemplary embodiment, the device may include silicone groin mold (simulated groin) (28), Shore hardness of 0010.

In an exemplary embodiment, the device may include high-temperature silicone rubber tubing (simulated femoral vein) (29) semi-clear blue, durometer 50 A, ⅜" inner diameter, ½" outer diameter, 25" in total length, 16" exposed on one end of silicone groin mold (simulated groin).

In an exemplary embodiment, the device may include high-temperature silicone rubber tubing (simulated femoral artery) (30) semi-clear white, durometer 50 A, 5/16" inner diameter, 7/16" outer diameter, 15" total length, 3¼" exposed on one end of silicone groin mold (simulated groin).

In an exemplary embodiment, the device may include in-line hose barb coupling insert (31) ⅜" inner diameter In an exemplary embodiment, the device may include clamp-style pinch valve (fourth conduit valve) (32).

In an exemplary embodiment, the device may include clamp-style pinch valve (fluid pressure source valve) (33).

In an exemplary embodiment, the device may include high-temperature silicone rubber tubing (fluid pressure source conduit) (34) semi-clear white, durometer 50 A, 5/16" inner diameter, 7/16" outer diameter.

In an exemplary embodiment, the device may include silicone tubing (main conduit) (35), ¾: inner diameter, 1" outer diameter, total length 42 cm.

In an exemplary embodiment, the device may include proximal "Zone 1" branch tubing (first conduit) (36), high-temperature silicone rubber tubing, 3/16" inner diameter, 5/16" outer diameter, 28" in length.

In an exemplary embodiment, the device may include proximal "Zone 2" branch tubing (one of the second conduit bifurcations) (37), high-temperature silicone rubber tubing, 3/16" inner diameter, 5/16" outer diameter, 8" in length, originating 4½" proximal to component 39 at medial aspect of component 14.

In an exemplary embodiment, the device may include distal "Zone 2" branch tubing (the other of the second conduit bifurcations) (38), high-temperature silicone rubber tubing, 3/16" inner diameter, 5/16" outer diameter, 9" in length, originating 3" proximal to component 39 at medial aspect of simulated vertebra L2.

In an exemplary embodiment, the device may include bifurcation point (simulated aortic bifurcation) (39) of component 35 with reduction of inner diameter from ¾" to ⅝", placed lateral to component 2 (simulated vertebral column) at position between simulated vertebrae L3 and L4.

In an exemplary embodiment, the device may include in-line hose barb coupling body (40) ⅜" inner diameter.

In an exemplary embodiment, the device may include "Zone 3" branch tubing (third conduit) (41), high-temperature silicone rubber tubing, 3/16" inner diameter, 5/16" outer diameter, 12" in length.

In an exemplary embodiment, the device may include combined "Zone 2" branch tubing (second conduit) (42), high-temperature silicone rubber tubing, 3/16" inner diameter, 5/16" outer diameter, 10" in length.

In an exemplary embodiment, the device may include clamp-style pinch valve (third conduit valve) (43).

In an exemplary embodiment, the device may include clamp-style pinch valve (second conduit valve) (44).

In an exemplary embodiment, the device may include clamp-style pinch valve (first conduit valve) (45).

In an exemplary embodiment, the device may include inflow fluid reservoir (fluid pressure source) (46) with volume capacity of 3000 milliliters or greater.

In an exemplary embodiment, the device may include outflow reservoir tubing (fluid collection reservoir conduit) (47), polyvinyl chloride/polyurethane clear tubing, 5/16" inner diameter, 7/16" outer diameter.

In an exemplary embodiment, the device may include outflow fluid reservoir (fluid collection reservoir) (48) with volume capacity of 5000 milliliters or greater.

In an exemplary embodiment, the device may include mannequin outer body (49), hollow, of appropriate proportion to mimic the size of a human from the neck to the mid-thigh and mid-arm.

In an exemplary embodiment, the device may include central aperture (50) in component 49.

Figure 2A:
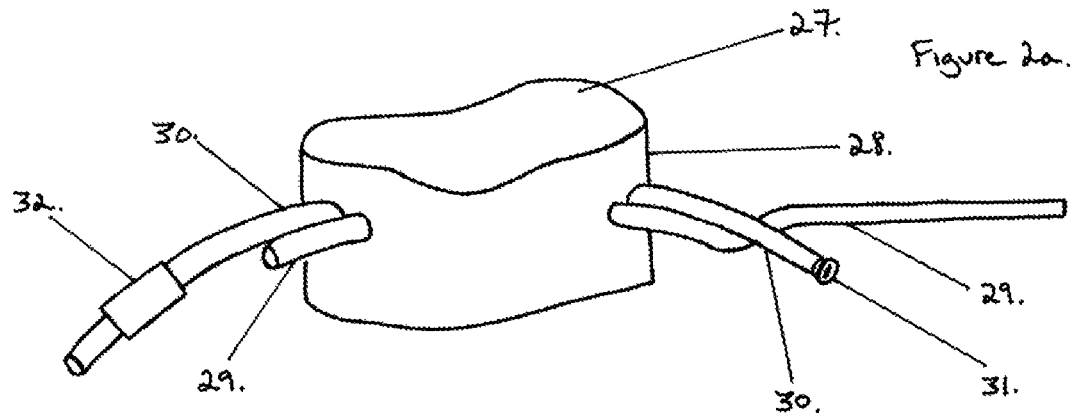
FIG. 2a depicts an oblique view of an embodiment of a groin mold (simulated groin) with embedded tubing according to the present disclosure.
Figure 2B:
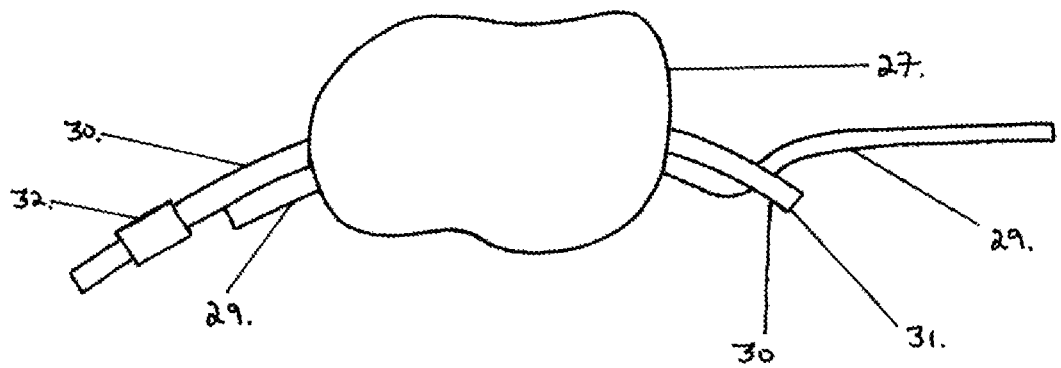
FIG. 2b depicts a top-down view of an embodiment of a groin mold (simulated groin) with embedded tubing according to the present disclosure.
Figure 3:
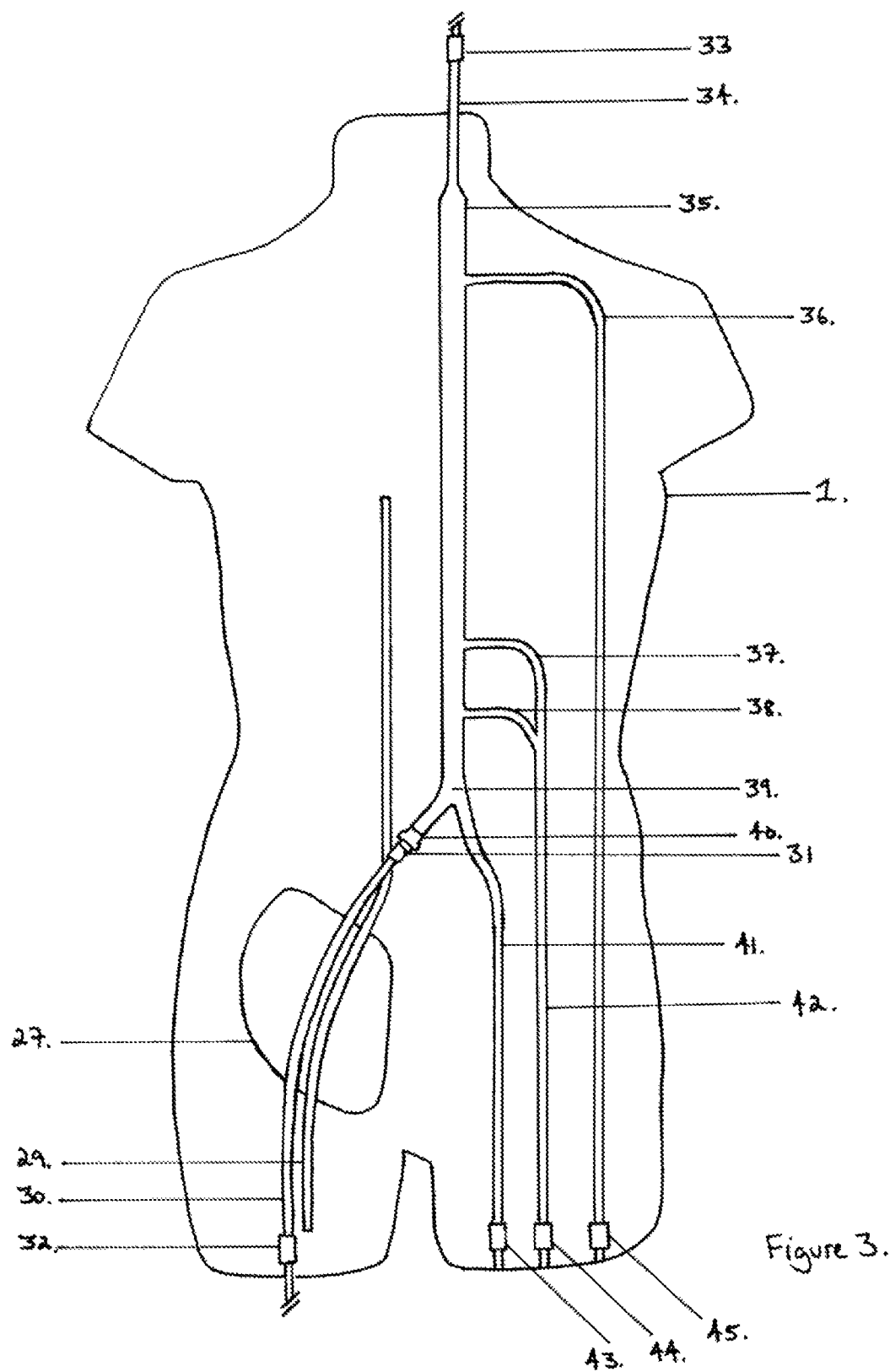
FIG. 3 depicts an embodiment of inflow and outflow tubing (conduits) with a groin mold (simulated groin) inset according to the present disclosure.
Figure 4:
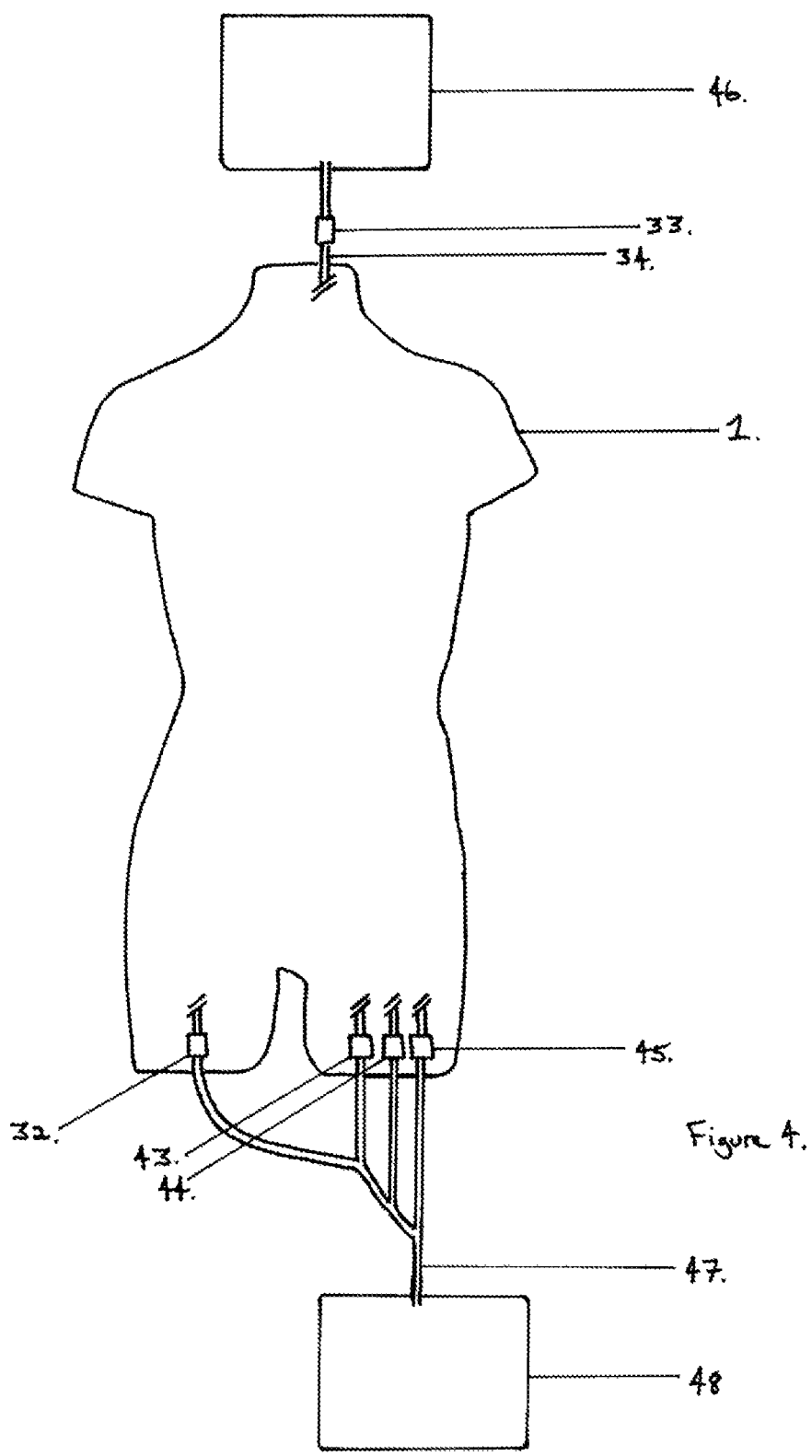
FIG. 4 depicts an embodiment of inflow (fluid pressure source) and outflow (fluid collection) reservoirs according to the present disclosure.
Figure 5:
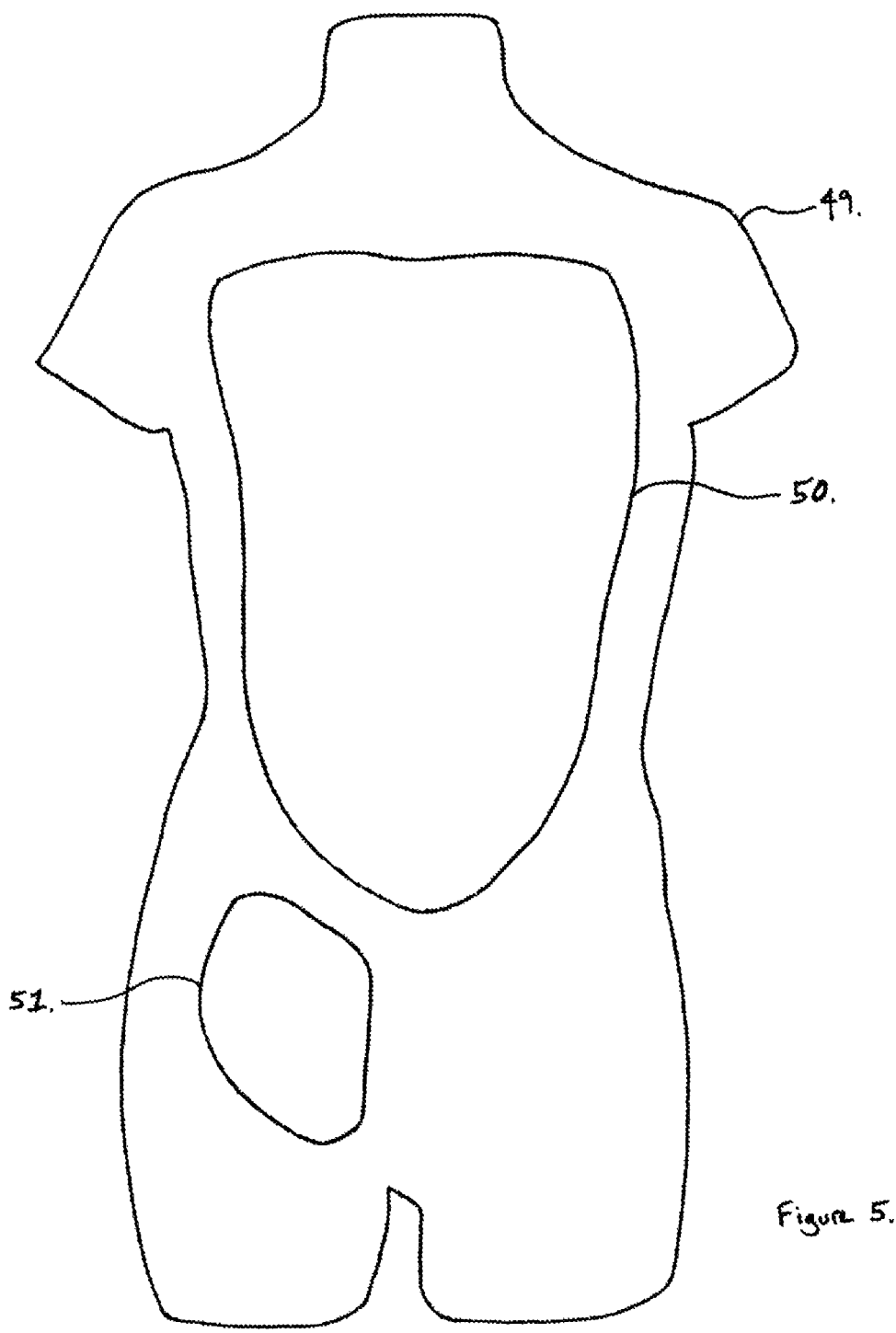
FIG. 5. depicts an embodiment of the periphery of a model housing according to the present disclosure.
Figure 6:
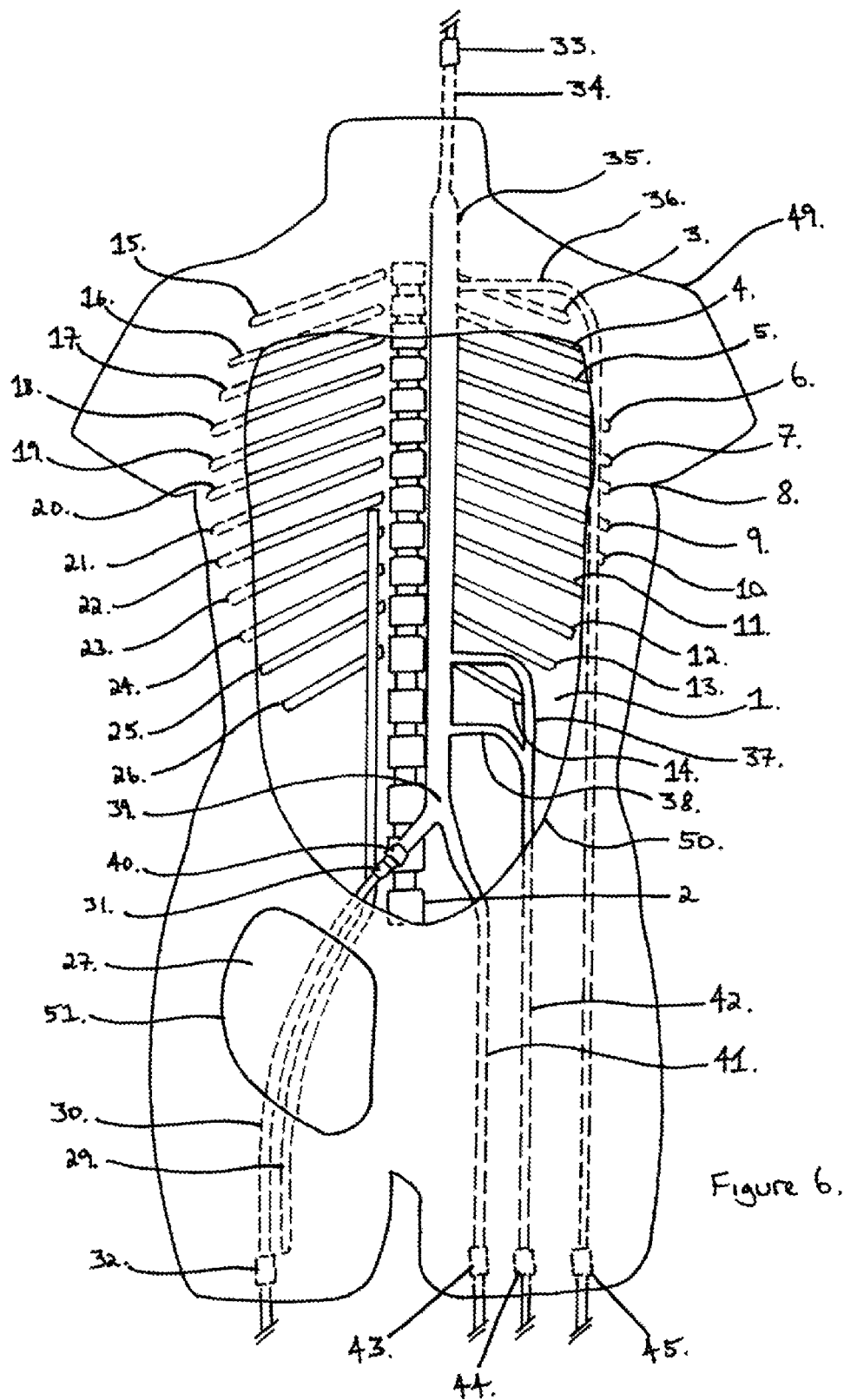
FIG. 6 depicts an embodiment of an assembled apparatus according to the present disclosure.
Figure 7:
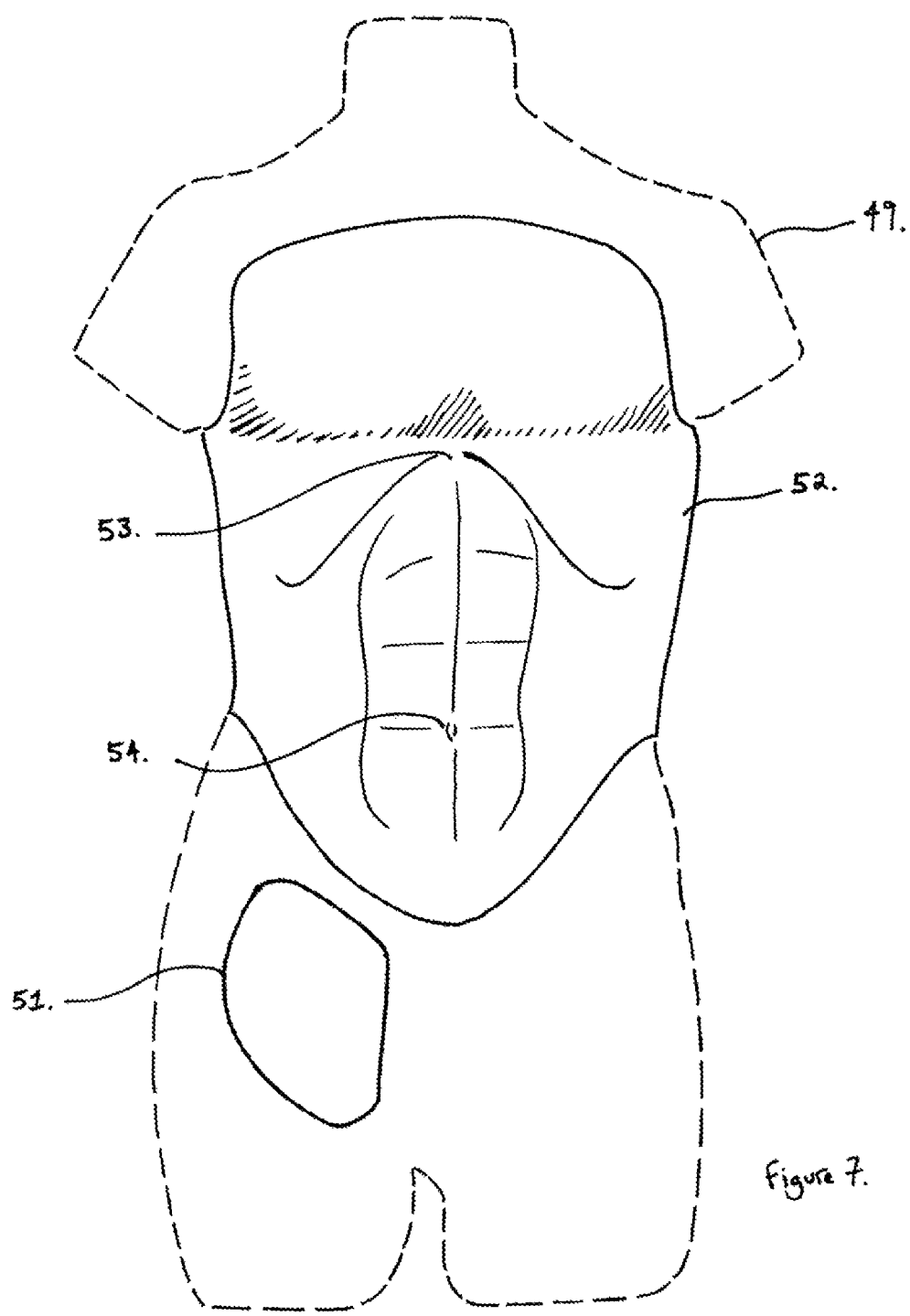
FIG. 7 depicts an embodiment of the central portion of a model housing according to the present disclosure.

In an exemplary embodiment, the device may include peripheral aperture (51) to allow placement of component 27 as shown in FIG. 2a and FIG. 2b.

In an exemplary embodiment, the device may include anterior chest wall (radiolucent surface of torso portion) (52) of mannequin to obscure view of an embodiment through component 50. Surface of this component is shaped so as to mimic the chest of a human.

In an exemplary embodiment, the device may include upper midline point (53) of component 52, centered between medial aspects of components 12 and 24, corresponding to xiphoid process of an adult man at vertebral level T10.

In an exemplary embodiment, the device may include lower midline point (53) of component 52, centered over component 2 at level of component 39, corresponding to umbilicus of a human at vertebral level L3.

In an exemplary embodiment, the components of the device may be assembled as follows. Components 2-26 may be bonded to component 1 in position as shown in FIG. 1. Components 29 and 30 may be embedded in component 28 as shown in FIG. 2a. Component 31 may be inserted into proximal end of component 30 to allow joining of component 30 to component 39 through component 40. Component 32 may be inserted over the distal portion of component 32. Component 33 may be inserted over the proximal portion of component 34. Component 34 may be joined to component 35 by smooth taper or as separate elements through use of an inline tube reducer (not shown). Components 36-38 may be directly bonded to component 35. Component 39 may be accomplished through an inline reducing Wye (not shown). Component 40 may be inserted into the distal end of component 39 on the side with component 27. Components 37 and 38 may be bonded together to form component 42. This may be accomplished through manufacturing as a single piece or through the use of a joining Wye (not shown). Component 39 may taper to become component 41. Alternatively, component 41 may be joined to component 39 with an inline reducer (not shown). Components 32, 43-45 may be inserted over components 30, 41, 42, and 36 respectively. Component 46 may be connected to component 34. Component 47 may be connected to components 30, 41, 42, 36 and 48. Component 49 may be connected to component 1 along its margin. Component 28 may be placed into component 51. Component 52 may be connected to component 49 in order to obscure component 50.

In an exemplary embodiment, the device may be set up as follows. Components 32, 33, 43, 44, and 45 may be placed in a closed position. Component 52 may be removed from component 49 to allow inspection of components 35, 37, 38, 39, 41, and 42. Component 28 may be placed into component 51. Component 31 may be connected to component 40. Component 29 may be filled with fluid. Component 46 may be filled with 3000 milliliters of fluid and raised to a height 12 feet above level of component 1. Component 33 may be opened to allow filling of component 35 with fluid and evacuation of gas into component 46. Components 32, 43, 44, and 45 may be opened and closed briefly to allow fluid to fill components 30, 36, 37, 38, 41, and 42. With full evacuation of air from components 30, 36, 35, 37, 38, 41, and 42, components 32, 33, 43, 44, and 45 may be placed in a closed position. Component 52 may be replaced onto component 49. Component 45 may be opened to allow fluid to leave the disclosed embodiment through component 36. This may be done to simulate the clinical scenario of hemorrhage from an injury to an arterial vessel in the human thorax, or "Zone 1". While component 33 is in the closed position, no fluid can flow from the disclosed embodiment. Component 44 may be opened to allow fluid to leave the disclosed embodiment through component 42. This may be done to simulate the clinical scenario of hemorrhage from an injury to an arterial vessel in the human abdomen, or "Zone 2". While component 33 is in the closed position, no fluid can flow from the disclosed embodiment. Component 43 may be opened to allow fluid to leave the disclosed embodiment through component 41. This is done to simulate the clinical scenario of hemorrhage from an injury to an arterial vessel in the pelvis, or "Zone 3". While component 33 is in the closed position, no fluid can flow from the disclosed embodiment. Component 33 may be placed in the open position, allowing fluid to flow from component 46 through components 34 and 35, and drain into component 48. The path the fluid takes for drainage is dependent upon which of the components 43, 44, and/or 45 is in the open position.

In an exemplary embodiment, the disclosed embodiment may be operated according to the following disclosure. Clinically relevant zones of hemorrhage from trauma to the Thorax, Abdomen, or Pelvis are defined as follows: Zone 1: Hemorrhage from Thoracic injury, simulated by fluid flow through component 36. Zone 1 exists proximally from medial aspects of components 3 and 15 and distally to medial aspects of components 13 and 25. This correlates to Thoracic injury between vertebral body levels T1 and T11. Zone 2: Hemorrhage from Abdominal injury, simulated by fluid flow through component 42. Zone 2 exists proximally from component 37 and distally from component 38. This correlates to Abdominal injury between vertebral body levels T12 and L2. Zone 3: Hemorrhage from Pelvic or lower extremity injury, simulated by fluid flow through component 30 or component 41. Zone 3 exists distally from component 38. This correlates to Pelvic or lower extremity injury distal to vertebral body level L2.

In an exemplary embodiment, the disclosed embodiment may begin to simulate Thoracic, Abdominal, or Pelvic hemorrhage beginning with the placement of component 33 in the open position. The falling fluid level visible in component 46 may provide an analog indication of the rate of fluid loss (or hemorrhage) and an approximation of the time remaining prior to the volume of fluid in component 46 becoming exhausted as it drains into component 48. The fluid level in component 46 may stop once a balloon catheter is inflated and successfully occludes the flow of fluid into component 48.

In an exemplary embodiment, a balloon catheter may be inflated at the position of component 39, causing the flow of fluid from component 46 to components 30 and 41 to decrease and stop. This mimics the placement of a balloon catheter to stop hemorrhage from a "Zone 3" injury.

In an exemplary embodiment, a balloon catheter may be inflated between component 38 and 37, in which case the flow of fluid from component 46 to component 42 will continue. This mimics the placement of a balloon catheter to partially stop hemorrhage from a "Zone 2" injury. A balloon catheter may be inflated between component 37 and 36, causing the flow of fluid from component 46 to component 42 to decrease and stop. This mimics the placement of a balloon catheter to completely stop hemorrhage from a "Zone 2" injury.

In an exemplary embodiment, balloon catheters cannot be placed between component 36 and 35. This mimics the continued hemorrhage of a "Zone 1" thoracic injury.

In an exemplary embodiment, the device may be utilized to simulate direct percutaneous access. The person using the simulator (hereafter described as USER) may introduce an eighteen gauge needle through component 28 into component 30. Fluid within component 30 may exit the needle, confirming position of the needle within the lumen of component 30. A 0.035" diameter wire may then be inserted through the eighteen gauge needle into component 30. The wire may continue on its course through components 31, 40 and 39 into component 35. The eighteen gauge needle may be removed, leaving the wire in place. A surgical scalpel may be used to incise component 28 for one centimeter contiguous with the entry point of the wire. The portion of the wire external to component 30 may then be placed into the lumen of a dilator and sheath and the dilator and sheath may be advanced upon the wire through component 28 and into component 30. The dilator may be removed from within the sheath while the sheath and wire remain. The portion of the wire external to the sheath may then be introduced into the lumen of a catheter with a balloon component. The balloon catheter may then be advanced along the course of the wire into the sheath, through component 28, into component 30 until it reaches component 39. The balloon may then be inflated with radio-opaque fluid.

In an exemplary embodiment, if the USER is unable to introduce the eighteen gauge needle through component 28 into component 30, an ultrasound probe may be used to identify components 29 and 30 within component 30. With identification of component 30 in a position lateral to component 29 on ultrasound imaging, the USER may proceed as described with respect to direct percutaneous access.

In an exemplary embodiment, if the USER is unable to introduce the eighteen gauge needle through component 28 into component 30 with the assistance of ultrasound, components 29 and 30 may be accessed by directly cutting component 28 with a surgical scalpel, separating the layers of silicone until component 30 may be seen and may be directly entered with a needle or scalpel. With identification of component 30, the USER may proceed as described with respect to direct percutaneous access.

In an exemplary embodiment, position of balloon catheter may be examined by use of roentgenogram or fluoroscopy when the balloon is inflated with radio-opaque material. The sections of component 2 as well as the positions of components 3-26 may indicate the vertebral levels which correspond to the positions of components 37, 38, and 39.

In an exemplary embodiment, measuring the distance from the center of component 28 to component 53 may approximate the distance that the balloon catheter needs to be inserted prior to inflation to ensure occlusion of component 35 above Zone 2. Measuring the distance from the center of component 28 to component 54 may approximate the distance that the balloon catheter needs to be inserted prior to inflation to ensure occlusion of component 35 below Zone 2 and above component 39.

In an exemplary embodiment, after a single use of the simulator, component 46 may be filled with the fluid from component 48 by placing component 46 in a dependent position to component 48.

In an exemplary embodiment, the device may simulate thoracic-, abdominal-, or two types of pelvic-hemorrhage, either in tandem or isolation.

In an exemplary embodiment, the device may simulate "real world" hemorrhages for the USER, allowing training for expert placement of a balloon catheter.

In an exemplary embodiment, the surface anatomy of the device may be correlated with vascular anatomy, skeletal anatomy and/or radiographic anatomy.

In an exemplary embodiment the device may contain no metal allowing for complete assessment of balloon catheter positioning radiographically.

In an alternative embodiment, components 30, 36, 41, and 42 may be connected to separate draining reservoirs.

In an alternative embodiment, pressure monitoring may be performed at components 30, 36, 41, and 42 to provide an additional measure of balloon occlusion.

In an alternative embodiment, tubing (conduits) may be of any length, internal diameter, or external diameter.

In an alternative embodiment, valves may be variable or not, one-way or two-way.

In an alternative embodiment, reservoirs may be of any volume.

In an alternative embodiment, radio-opacity may be accomplished with alternative materials, including paint.

In an alternative embodiment, component 32 and 34 may be connected to the outflow and inflow ports of a fluid pump, respectively, to allow higher pressures to be achieved within the disclosed embodiment and to simulate human arterial pressure waveforms.

In an alternative embodiment, components 1-26 may be manufactured from a single casted object.

In an alternative embodiment, component 30 may be used for the training of arterial catheter placement, and may be performed without the need for placement of a balloon catheter.

In an alternative embodiment, component 29 may be used for the training of central venous catheter placement, and may be performed without the need for identification as a landmark.

Example 1

A procedural simulation device having a radiopaque framework for mimicking the appearance of a skeleton on roentgenogram (xray) or fluoroscopy. The device may have a radio-opaque representation of thoracic (T1-T12) and lumbar (L1-L5) vertebral bodies, a radio-opaque representation of thoracic ribs (3-26), a central tubing system mounted to said framework for mimicking the arterial system. Said arterial system mimic may have a large diameter compliant tubing for the human aorta (35), small diameter branch tubing to mimic vessel of the thoracic aorta, small diameter branch tubing to mimic proximal and distal vessels of the abdominal aorta, small diameter branch tubing to mimic common iliac and femoral vessels of the human pelvis.

Flow control valves (43-45) may be provided to control fluid flow through tubing system to mimic arterial hemorrhage in one or more zones. The system further may have a proximal fluid reservoir (46) with adjustable flow rate and a distal fluid reservoir (48) for collection of fluid from simulated hemorrhage.

The fluid control valves may be arranged between proximal and distal fluid reservoirs to direct flow through branch tubing of thoracic aorta (36), abdominal aorta (42), or pelvic conduits (41). Access to tubing systems may be through a block of silicone or gelatin of appropriate color and hardness to mimic tissue (27-28). Tubing may be embedded within the block of silicone or gelatin to mimic the anatomical position of the femoral artery (30) and femoral vein (29). There may be a femoral artery tubing connecting to the central tubing system.

The device may also have a mannequin torso (49, 50, and 52-54) to cover the above components with surface anatomy mimicking a torso. Said mannequin torso may have a neck, pectoralis major muscles, shoulders, upper arms, sternum and xiphoid, lower costal margins, abdominal wall and musculature, umbilicus, pelvic brim, pubic tubercle, inguinal ligaments, and upper legs.

A balloon catheter may be placed from an external position into the central tubing system (27-30). Inflation of the balloon catheter may occlude the flow of fluid from the proximal reservoir to the distal reservoir. Entry of the balloon catheter into the central tubing system may be achieved through direct needle access, ultrasound-guided needle access, and/or open surgical access (cut down).

A balloon catheter can be selectively positioned in the central tubing system. The position of the balloon catheter may be confirmed by roentgenogram (x-ray) or fluoroscopy. Radiographic markers of the device may correlate to the positions of the central tubing system's branches, mimicking clinically relevant scenarios of hemorrhage control. The surface anatomy (53-54) of the mannequin may provide landmarks for the positioning of the balloon catheter. Several scenarios of hemorrhage from different positions along the aorta may be simulated: hemorrhage from the thoracic aorta, the abdominal aorta, and/or the pelvic vessels.

The rate of fluid flow from proximal to distal fluid reservoirs may correlate to rates of major arterial injury. Analog signals of control of hemorrhage may be relayed to the user. Balloon occlusion of the central tubing system may result in a static level of fluid in the proximal reservoir. Balloon occlusion of the central tubing system may be confirmed with direct visualization. Balloon occlusion of the aorta may be confirmed with injection of radiopaque dye during fluoroscopy. Radiographic landmarks, surface landmarks, and arterial systems branch points may be correlated to each other.

Example 2

A surgical simulator is in the form of a mannequin with a torso portion (1). The torso portion may have a simulated vertebral column (2) with twelve thoracic vertebrae (T1-T12) and five lumbar vertebrae (L1-L5). The torso portion may also have a plurality of anatomical aortic zones for the REBOA procedure, the first zone being defined by a first area extending caudally from a first thoracic vertebra (T1) to an eleventh thoracic vertebra (T11), the second zone being defined by a second area extending caudally from the eleventh thoracic vertebra (T11) to a second lumbar vertebra (L2).

The surgical simulator may have a fluid pressure source (46) that may be adapted and configured to provide a fluid to the torso portion. The surgical simulator may have a fluid collection reservoir (48) that may be adapted and configured to receive fluid from the torso portion.

The surgical simulator may have a main conduit (35) that may be operatively connected with the fluid pressure source and may extend through the first and second zones. The main conduit may be adapted and configured to simulate the aorta.

The surgical simulator may have a fluid pressure source valve (33) that may be operatively connected with the main conduit and the fluid pressure source. The fluid pressure source valve may be movable between an open position in which the fluid from the fluid pressure source flows through the main conduit and the first and second zones, and a closed position in which the fluid from the fluid pressure source is prevented from flowing through the main conduit and the first and second zones.

The surgical simulator may have a first conduit (36) that may be operatively connected with the main conduit (35) in the first zone and in communication therewith. The first conduit may have a first conduit valve (45) that may be movable between an open position allowing fluid to flow through the main conduit and the first conduit to the fluid collection reservoir to simulate an injury in the first zone, and a closed position to prevent fluid from flowing through the first conduit to the fluid collection reservoir to simulate no injury in the first zone.

The surgical simulator may have a second conduit (42) that may have a bifurcated portion that may be operatively connected with the main conduit in the second zone and in communication therewith. The second conduit may have a second conduit valve (44) that may be movable between an open position allowing fluid to flow through the main conduit and the second conduit bifurcations and the second conduit to the fluid collection reservoir to simulate an injury in the second zone, and a closed position to prevent fluid from flowing through the second conduit bifurcations and the second conduit to the fluid collection reservoir to simulate no injury in the second zone.

The surgical simulator may have a simulated groin (27-28) portion that may be adapted and configured to receive a REBOA catheter. The simulated groin portion may have a fourth conduit (30) that may extend therethrough. The fourth conduit may be adapted and configured to simulate the femoral artery. The fourth conduit may be operatively connected with the main conduit and in communication therewith and may simulate an aortic bifurcation (39) at a position that may correspond to the third lumbar vertebra (L3), thereby potentially allowing the REBOA catheter to lodge a balloon in the main conduit in the first and the second zones. The fourth conduit may be in communication with the fluid collection reservoir.

The surgical simulator may have a fourth conduit valve (32) that may be positionable between a closed position in which the fluid is prevented from flowing through the main conduit and the fourth conduit, and an open position allowing fluid flow from main conduit through the fourth conduit to the fluid collection reservoir.

In another aspect of the surgical simulator, the torso portion may also have simulated ribs (3-26) that may anatomically correspond to the respective vertebra.

In another aspect of the surgical simulator, the simulated vertebrae and ribs may be at least semi radiopaque.

In another aspect of the surgical simulator, one of the second conduit bifurcations (37) may connect with the main conduit at a position that may correspond to the twelfth thoracic vertebra (T12). The other of the second conduit bifurcations (38) may connect with the main conduit at a position that may correspond to the second lumbar vertebra (L2). Said other second conduit bifurcation may be adapted and configured to anatomically simulate positioning of the renal arteries.

In another aspect of the surgical simulator, the simulated groin may also have a fifth conduit (29). The fifth conduit may be anatomically positioned adjacent to the simulated femoral artery and may be adapted and configured to simulate a femoral vein.

In another aspect of the surgical simulator, the torso may also have a radiolucent surface of said torso portion (49, 50, and 52-54). Said surface may be adapted and configured to simulate skin anatomically covering said torso portion.

Example 3

A surgical simulator is in the form of a mannequin with a torso portion (1). The torso portion may have a simulated vertebral column (2) with twelve thoracic vertebrae (T1-T12) and five lumbar vertebrae (L1-L5). The torso portion may also have a plurality of anatomical aortic zones for the REBOA procedure, the second zone being defined by a second area extending caudally from the eleventh thoracic vertebra (T11) to a second lumbar vertebra (L2), the third zone being defined by a third area extending caudally from the second lumbar vertebrae (L2) to a fifth lumbar vertebra (L5).

The surgical simulator may have a fluid pressure source (46) that may be adapted and configured to provide a fluid to the torso portion. The surgical simulator may have a fluid collection reservoir (48) that may be adapted and configured to receive fluid from the torso portion.

The surgical simulator may have a main conduit (35) that may be operatively connected with the fluid pressure source and may extend through the second and third zones. The main conduit may be adapted and configured to simulate the aorta.

The surgical simulator may have a fluid pressure source valve (33) that may be operatively connected with the main conduit and the fluid pressure source. The fluid pressure source valve may be movable between an open position in which the fluid from the fluid pressure source flows through the main conduit and the second and third zones, and a closed position in which the fluid from the fluid pressure source is prevented from flowing through the main conduit and the second and third zones.

The surgical simulator may have a second conduit (42) that may have a bifurcated portion that may be operatively connected with the main conduit in the second zone and in communication therewith. The second conduit may have a second conduit valve (44) that may be movable between an open position allowing fluid to flow through the main conduit and the second conduit bifurcations and the second conduit to the fluid collection reservoir to simulate an injury in the second zone, and a closed position to prevent fluid from flowing through the second conduit bifurcations and the second conduit to the fluid collection reservoir to simulate no injury in the second zone.

The surgical simulator may have a third conduit (41) that may be operatively connected with the main conduit in the third zone and in communication therewith. The third conduit connection with the main conduit may be adapted and configured to simulate an aortic bifurcation (39) and may be at a position corresponding to the third lumbar vertebra (L3). The third conduit may simulate an iliac artery and femoral artery. The third conduit may have a third conduit valve (43) that may be movable between an open position allowing fluid to flow through the main conduit and the third conduit to the fluid collection reservoir to simulate an injury in the third zone, and a closed position to prevent fluid from flowing through the third conduit to the fluid collection reservoir to simulate no injury in the third zone;

The surgical simulator may have a simulated groin (27-28) portion that may be adapted and configured to receive a REBOA catheter. The simulated groin portion may have a fourth conduit (30) that may extend therethrough. The fourth conduit may be adapted and configured to simulate the femoral artery. The fourth conduit may be operatively connected with the main conduit and in communication therewith and may simulate an aortic bifurcation (39) at a position that may correspond to the third lumbar vertebra (L3), thereby potentially allowing the REBOA catheter to lodge a balloon in the main conduit in the second and the third zones. The fourth conduit may be in communication with the fluid collection reservoir.

The surgical simulator may have a fourth conduit valve (32) that may be positionable between a closed position in which the fluid is prevented from flowing through the main conduit and the fourth conduit, and an open position allowing fluid flow from main conduit through the fourth conduit to the fluid collection reservoir.

In another aspect of the surgical simulator, the torso portion may also have simulated ribs (3-26) anatomically corresponding to the respective vertebra.

In another aspect of the surgical simulator, the simulated vertebrae and ribs may be at least semi radiopaque.

In another aspect of the surgical simulator, one of the second conduit bifurcations (37) may connect with the main conduit at a position corresponding to the twelfth thoracic vertebra (T12). The other of the second conduit bifurcations (38) may connect with the main conduit at a position corresponding to the second lumbar vertebra (L2), said other second conduit bifurcation may be adapted and configured to anatomically simulate positioning of the renal arteries.

In another aspect of the surgical simulator, the simulated groin may also have a fifth conduit (29). The fifth conduit may be anatomically positioned adjacent to the simulated femoral artery and may be adapted and configured to simulate a femoral vein.

In another aspect of the surgical simulator, the torso may also have a radiolucent surface of said torso portion (49, 50, and 52-54), and said surface may be adapted and configured to simulate skin anatomically covering said torso portion.

Example 4

A surgical simulator is in the form of a mannequin with a torso portion (1). The torso portion may have a simulated vertebral column (2) with twelve thoracic vertebrae (T1-T12) and five lumbar vertebrae (L1-L5). The torso portion may also have a plurality of anatomical aortic zones for the REBOA procedure, the first zone being defined by a first area extending caudally from a first thoracic vertebra (T1) to an eleventh thoracic vertebra (T11), the second zone being defined by a second area extending caudally from the eleventh thoracic vertebra (T11) to a second lumbar vertebra (L2).

The surgical simulator may have a fluid pressure source (46) that may be adapted and configured to provide a fluid to the torso portion. The surgical simulator may have a fluid collection reservoir (48) that may be adapted and configured to receive fluid from the torso portion.

The surgical simulator may have a main conduit (35) that may be operatively connected with the fluid pressure source and may extend through the first, second, and third zones. The main conduit may be adapted and configured to simulate the aorta.

The surgical simulator may have a fluid pressure source valve (33) that may be operatively connected with the main conduit and the fluid pressure source. The fluid pressure source valve may be movable between an open position in which the fluid from the fluid pressure source flows through the main conduit and the first, second, and third zones, and a closed position in which the fluid from the fluid pressure source is prevented from flowing through the main conduit and the first, second, and third zones.

The surgical simulator may have a first conduit (36) that may be operatively connected with the main conduit (35) in the first zone and in communication therewith. The first conduit may have a first conduit valve (45) that may be movable between an open position allowing fluid to flow through the main conduit and the first conduit to the fluid collection reservoir to simulate an injury in the first zone, and a closed position to prevent fluid from flowing through the first conduit to the fluid collection reservoir to simulate no injury in the first zone.

The surgical simulator may have a second conduit (42) that may have a bifurcated portion that may be operatively connected with the main conduit in the second zone and in communication therewith. The second conduit may have a second conduit valve (44) that may be movable between an open position allowing fluid to flow through the main conduit and the second conduit bifurcations and the second conduit to the fluid collection reservoir to simulate an injury in the second zone, and a closed position to prevent fluid from flowing through the second conduit bifurcations and the second conduit to the fluid collection reservoir to simulate no injury in the second zone.

The surgical simulator may have a third conduit (41) that may be operatively connected with the main conduit in the third zone and in communication therewith. The third conduit connection with the main conduit may be adapted and configured to simulate an aortic bifurcation (39) and may be at a position corresponding to the third lumbar vertebra (L3). The third conduit may simulate an iliac artery and femoral artery. The third conduit may have a third conduit valve (43) that may be movable between an open position allowing fluid to flow through the main conduit and the third conduit to the fluid collection reservoir to simulate an injury in the third zone, and a closed position to prevent fluid from flowing through the third conduit to the fluid collection reservoir to simulate no injury in the third zone;

The surgical simulator may have a simulated groin (27-28) portion that may be adapted and configured to receive a REBOA catheter. The simulated groin portion may have a fourth conduit (30) that may extend therethrough. The fourth conduit may be adapted and configured to simulate the femoral artery. The fourth conduit may be operatively connected with the main conduit and in communication therewith and may simulate an aortic bifurcation (39) at a position that may correspond to the third lumbar vertebra (L3), thereby potentially allowing the REBOA catheter to lodge a balloon in the main conduit in the first, second, and the third zones. The fourth conduit may be in communication with the fluid collection reservoir.

The surgical simulator may have a fourth conduit valve (32) that may be positionable between a closed position in which the fluid is prevented from flowing through the main conduit and the fourth conduit, and an open position allowing fluid flow from main conduit through the fourth conduit to the fluid collection reservoir.

In another aspect of the surgical simulator, the torso portion may also have simulated ribs (3-26) that may anatomically correspond to the respective vertebra.

In another aspect of the surgical simulator, the simulated vertebrae and ribs may be at least semi radiopaque.

In another aspect of the surgical simulator, one of the second conduit bifurcations (37) may connect with the main conduit at a position that may correspond to the twelfth thoracic vertebra (T12). The other of the second conduit bifurcations (38) may connect with the main conduit at a position that may correspond to the second lumbar vertebra (L2). Said other second conduit bifurcation may be adapted and configured to anatomically simulate positioning of the renal arteries.

In another aspect of the surgical simulator, the simulated groin may also have a fifth conduit (29). The fifth conduit may be anatomically positioned adjacent to the simulated femoral artery and may be adapted and configured to simulate a femoral vein.

In another aspect of the surgical simulator, the torso may also have a radiolucent surface of said torso portion (49, 50, and 52-54). Said surface may be adapted and configured to simulate skin anatomically covering said torso portion.

While the disclosure has been described in connection with certain embodiments, this should not be taken as a limitation to all of the provided details. Modifications and variations of the described embodiments may be made without departing from the spirit and scope of the disclosed embodiments, and other embodiments should be understood to be encompassed in the present disclosure as would be understood by those of ordinary skill in the art.

What is claimed is:

1. A surgical simulator comprising:
   a mannequin comprising a torso portion, the torso portion comprising a simulated vertebral column with twelve thoracic vertebrae and five lumbar vertebrae, the torso portion comprising a plurality of anatomical aortic zones for a REBOA procedure, the first zone being defined by a first area extending caudally from a first thoracic vertebra to an eleventh thoracic vertebra, the second zone being defined by a second area extending caudally from the eleventh thoracic vertebra to a second lumbar vertebra;
   a fluid pressure source being adapted and configured to provide a fluid to the torso portion;
   a fluid collection reservoir being adapted and configured to receive fluid from the torso portion;
   a main conduit operatively connected with the fluid pressure source and extending through the first and second zones, the main conduit being adapted and configured to simulate the aorta;
   a fluid pressure source valve operatively connected with the main conduit and the fluid pressure source, the fluid pressure source valve being movable between an open position in which the fluid from the fluid pressure source flows through the main conduit and the first and second zones, and a closed position in which the fluid from the fluid pressure source is prevented from flowing through the main conduit and the first and second zones,
   a first conduit operatively connected with the main conduit in the first zone and in communication therewith, the first conduit having a first conduit valve movable between an open position allowing fluid to flow through the main conduit and the first conduit to the fluid collection reservoir to simulate an injury in the first zone, and a closed position to prevent fluid from flowing through the first conduit to the fluid collection reservoir to simulate no injury in the first zone;

a second conduit having a bifurcated portion operatively connected with the main conduit in the second zone and in communication therewith, the second conduit having a second conduit valve movable between an open position allowing fluid to flow through the main conduit and the second conduit bifurcations and the second conduit to the fluid collection reservoir to simulate an injury in the second zone, and a closed position to prevent fluid from flowing through the second conduit bifurcations and the second conduit to the fluid collection reservoir to simulate no injury in the second zone;

a simulated groin portion being adapted and configured to receive a catheter, the simulated groin portion comprising a further conduit extending therethrough, the further conduit being adapted and configured to simulate the femoral artery, the further conduit being operatively connected with the main conduit and in communication therewith and simulating an aortic bifurcation at a position corresponding to the third lumbar vertebra, thereby allowing the catheter to lodge a balloon in the main conduit in the first and the second zones, the further conduit being in communication with the fluid collection reservoir; and a further conduit valve positionable between a closed position in which the fluid is prevented from flowing through the main conduit and the further conduit, and an open position allowing fluid flow from main conduit through the further conduit to the fluid collection reservoir.

2. The surgical simulator according to claim 1, wherein the torso portion further comprises simulated ribs anatomically corresponding to the respective vertebra.

3. The surgical simulator according to claim 2, wherein the simulated vertebrae and ribs are at least semi radiopaque.

4. The surgical simulator according to claim 3, wherein one of the second conduit bifurcations connects with the main conduit at a position corresponding to the twelfth thoracic vertebra, and the other of the second conduit bifurcations connects with the main conduit at a position corresponding to the second lumbar vertebra, said other second conduit bifurcation being adapted and configured to anatomically simulate positioning of the renal arteries.

5. The surgical simulator according to claim 4, wherein the simulated groin further comprises a second further conduit, the second further conduit being anatomically positioned adjacent to the simulated femoral artery and adapted and configured to simulate a femoral vein.

6. The surgical simulator according to claim 5, the torso further comprising a radiolucent surface of said torso portion, said surface being adapted and configured to simulate skin anatomically covering said torso portion.

7. A surgical simulator comprising:
a mannequin comprising a torso portion, the torso portion comprising a simulated vertebral column with twelve thoracic vertebrae and five lumbar vertebrae, the torso portion comprising a plurality of anatomical aortic zones for a REBOA procedure, the second zone being defined by a second area extending caudally from the eleventh thoracic vertebra to the second lumbar vertebra, the third zone being defined by a third area extending caudally from the second lumbar vertebrae to a fifth lumbar vertebra;
a fluid pressure source being adapted and configured to provide pressurized fluid to the torso portion;
a fluid collection reservoir being adapted and configured to receive fluid from the torso portion,
a main conduit operatively connected with the fluid pressure source and extending through the second and third zones, the main conduit being adapted and configured to simulate the aorta;
a fluid pressure source valve operatively connected with the main conduit and the fluid pressure source, the fluid pressure source valve being movable between an open position in which the fluid from the fluid pressure source flows through the main conduit and the second and third zones, and a closed position in which the fluid from the fluid pressure source is prevented from flowing through the main conduit and the second and third zones;
a further conduit having a bifurcated portion operatively connected with the main conduit in the second zone and in communication therewith, the further conduit having a further conduit valve movable between an open position allowing fluid to flow through the main conduit and the further conduit bifurcations and the further conduit to the fluid collection reservoir to simulate an injury in the second zone, and a closed position to prevent fluid from flowing through the further conduit bifurcations and the further conduit to the fluid collection reservoir to simulate no injury in the second zone,
a second further conduit operatively connected with the main conduit in the third zone and in communication therewith, the second further conduit connection with the main conduit adapted and configured to simulate an aortic bifurcation at a position corresponding to the third lumbar vertebra, the second further conduit simulating an iliac artery and femoral artery, the second further conduit having a second further conduit valve movable between an open position allowing fluid to flow through the main conduit and the second further conduit to the fluid collection reservoir to simulate an injury in the third zone, and a closed position to prevent fluid from flowing through the second further conduit to the fluid collection reservoir to simulate no injury in the third zone;
a simulated groin adapted and configured to receive a catheter and comprising a third further conduit extending therethrough, the third further conduit being adapted and configured to simulate a femoral artery, the third further conduit being operatively connected with the main conduit and in communication therewith and simulating an aortic bifurcation at a position corresponding to the third lumbar vertebra, thereby allowing the catheter to be placed in the main conduit in the second and the third zones, the third further conduit being in communication with the fluid collection reservoir; and
a third further conduit valve positionable between a closed position in which the fluid is prevented from flowing through the main conduit and the third further conduit, and an open position allowing fluid flow from main conduit through the third further conduit to the fluid collection reservoir.

8. The surgical simulator according to claim 7, wherein the torso portion further comprises simulated ribs anatomically corresponding to the respective vertebra.

9. The surgical simulator according to claim 8, wherein the simulated vertebrae and ribs are at least semi radiopaque.

10. The surgical simulator according to claim 9, wherein one of the further conduit bifurcations connects with the main conduit at a position corresponding to the twelfth thoracic vertebra, and the other of the further conduit bifurcations connects with the main conduit at a position corresponding to the second lumbar vertebra, said other further conduit bifurcation being adapted and configured to anatomically simulate positioning of the renal arteries.

11. The surgical simulator according to claim 10, wherein the simulated groin further comprises a fourth further conduit, the fourth further conduit being anatomically positioned adjacent to the simulated femoral artery and adapted and configured to simulate a femoral vein.

12. The surgical simulator according to claim 11, the torso further comprising a radiolucent surface of said torso portion, said surface being adapted and configured to simulate skin anatomically covering said torso portion.

13. A surgical simulator comprising:
a mannequin comprising a torso portion, the torso portion comprising a simulated vertebral column with twelve thoracic vertebrae and five lumbar vertebrae, the torso portion comprising a plurality of anatomical aortic zones for a REBOA procedure, the first zone being defined by a first area extending caudally from a first thoracic vertebra to an eleventh thoracic vertebra, the second zone being defined by a second area extending caudally from the eleventh thoracic vertebra to a second lumbar vertebra, the third zone being defined by a third area extending caudally from the second lumbar vertebra to a fifth lumbar vertebra;
a fluid pressure source being adapted and configured to provide pressurized fluid to the torso portion;
a fluid collection reservoir being adapted and configured to receive fluid from the torso portion;
a main conduit operatively connected with the fluid pressure source and extending through the first, second, and third zones, the main conduit being adapted and configured to simulate the aorta,
a fluid pressure source valve operatively connected with the main conduit and the fluid pressure source, the fluid pressure source valve being movable between an open position in which fluid from the fluid pressure source flows through the main conduit and the first, second, and third zones, and a closed position in which the fluid from the fluid pressure source is prevented from flowing through the main conduit and the first, second, and third zones;
a first conduit operatively connected with the main conduit in the first zone and in communication therewith, the first conduit having a first conduit valve movable between an open position allowing fluid to flow through the main conduit and the first conduit to the fluid collection reservoir to simulate an injury in the first zone, and a closed position to prevent fluid from flowing through the first conduit to the fluid collection reservoir to simulate no injury in the first zone;
a second conduit having a bifurcated portion operatively connected with the main conduit in the second zone and in communication therewith, the second conduit having a second conduit valve movable between an open position allowing fluid to flow through the main conduit and the second conduit bifurcations and the second conduit to the fluid collection reservoir to simulate an injury in the second zone, and a closed position to prevent fluid from flowing through the second conduit bifurcations and the second conduit to the fluid collection reservoir to simulate no injury in the second zone,
a third conduit operatively connected with the main conduit in the third zone and in communication therewith, the third conduit connection with the main conduit adapted and configured to simulate an aortic bifurcation at a position corresponding to the third lumbar vertebra, the third conduit simulating an iliac artery and femoral artery, the third conduit having a third conduit valve movable between an open position allowing fluid to flow through the main conduit and the third conduit to the fluid collection reservoir to simulate an injury in the third zone, and a closed position to prevent fluid from flowing through the third conduit to the fluid collection reservoir to simulate no injury in the third zone,
a simulated groin adapted and configured to receive a catheter and comprising a fourth conduit extending therethrough, the fourth conduit being adapted and configured to simulate a femoral artery, the fourth conduit being operatively connected with the main conduit and in communication therewith and simulating an aortic bifurcation at a position corresponding to the third lumbar vertebra, thereby allowing the catheter to be placed in the main conduit in the first, second, and the third zones, the fourth conduit being in communication with the fluid collection reservoir; and
a fourth conduit valve positionable between a closed position in which the fluid is prevented from flowing through the main conduit and the fourth conduit, and an open position allowing fluid flow from main conduit through the fourth conduit to the fluid collection reservoir.

14. The surgical simulator according to claim 13, wherein the torso portion further comprises simulated ribs anatomically corresponding to the respective vertebra.

15. The surgical simulator according to claim 14, wherein the simulated vertebrae and ribs are at least semi-radiopaque.

16. The surgical simulator according to claim 15, wherein one of the second conduit bifurcations connects with the main conduit at a position corresponding to the twelfth thoracic vertebra, and the other of the second conduit bifurcations connects with the main conduit at a position corresponding to the second lumbar vertebra, said other second conduit bifurcation being adapted and configured to anatomically simulate positioning of the renal arteries.

17. The surgical simulator according to claim 16, wherein the simulated groin comprises a fifth conduit, the fifth conduit being anatomically positioned adjacent to the simulated femoral artery and adapted and configured to simulate a femoral vein.

18. The surgical simulator according to claim 17, the torso further comprising a radiolucent surface of said torso portion, said surface being adapted and configured to simulate skin anatomically covering said torso portion.

* * * * *